United States Patent [19]
Chutjian et al.

[11] 4,158,775
[45] Jun. 19, 1979

[54] HIGH RESOLUTION THRESHOLD PHOTOELECTRON SPECTROSCOPY BY ELECTRON ATTACHMENT

[76] Inventors: Robert A. Frosch, Administrator of the National Aeronautics and Space Administration, with respect to an invention of Ara Chutjian, Los Angeles; Joseph M. Ajello, Arcadia, both of Calif.

[21] Appl. No.: 856,466

[22] Filed: Nov. 30, 1977

[51] Int. Cl.² .................... B01D 59/44; B01J 39/34
[52] U.S. Cl. .................... 250/423 P; 250/281; 250/282
[58] Field of Search .............. 250/281, 282, 283, 284, 250/288, 423 R, 424, 423 P; 204/DIG. 11

[56] References Cited
U.S. PATENT DOCUMENTS

| | | | |
|---|---|---|---|
| 3,521,054 | 7/1970 | Webb | 250/423 P |
| 3,626,181 | 12/1971 | Wernlund | 250/282 |
| 3,742,213 | 6/1973 | Cohen et al. | 250/282 |
| 3,987,302 | 10/1976 | Hurst et al. | 250/423 P |

Primary Examiner—Bruce C. Anderson
Attorney, Agent, or Firm—Monte F. Mott; John R. Manning; Paul F. McCaul

[57] ABSTRACT

A system for determining the stable energy levels of a species ion, of an atomic, molecular, or radical type, by application of ionizing energy of a predetermined level, such as through photoionization. The system adds a trapping gas to the gaseous species to provide a technique for detection of the energy levels. The electrons emitted from ionized species are captured by the trapping gas, only if the electrons have substantially zero kinetic energy. If the electrons have nearly zero energy, they are absorbed by the trapping gas to produce negative ions of the trapping gas that can be detected by a mass spectrometer. The applied energies (i.e. light frequencies) at which large quantities of trapping gas ions are detected, are the stable energy levels of the positive ion of the species. $SF_6$ and $CFCl_3$ have the narrowest acceptance bands, so that when they are used as the trapping gas, they bind electrons (to form negative ions) only when the electrons have very close to zero kinetic energy.

10 Claims, 3 Drawing Figures

HIGH RESOLUTION THRESHOLD PHOTOELECTRON SPECTROSCOPY BY ELECTRON ATTACHMENT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to apparatus for measuring energy levels and ionization potentials of atoms, molecules, and radicals.

The determination of the stable energy levels of any particular atom, molecule, or radical, including the ionization potential and energy levels above the ionization potential, is needed in a variety of applications. For example, knowledge about the stable enerby levels is important in choosing materials for use in ion lasers, and in modeling the earth's upper atmosphere. Previously, conventional photoelectron spectroscopic (PES) and threshold photoelectron spectroscopic (TPES) techniques have been used to measure the energy levels produced by photo ionization. However, techniques that were simpler to use and that provided even higher precision would be useful.

SUMMARY OF THE INVENTION

In accordance with the present invention, a system is provided for measuring the energy levels and ionization potential of a species (atom, molecule or radical), which enables the determination of the energy levels with high precision. Such measurement is accomplished by the use of a trapping gas which is mixed or otherwise placed in the vicinity of the species whose energy levels are to be determined. The species is then excited as by the application of light of a predetermined wavelength, so that photons of predetermined energy strike the molecules of the species to raise the species molecules to a predetermined energy state of its positive ion. Molecules energized above their ionization potential, produce electrons having kinetic energy equal to the difference between the energy state to which the molecule was raised and other lower stable energy states of that molecule. Only if the molecule was raised close to the threshold of a stable energy state, will the emitted electrons have nearly zero energy, and only then will the electrons be absorbed by a trapping gas that absorbs only electrons of substantially zero energy. The trapping gas molecules which absorb an electron can be detected in a mass spectrometer. Thus, for any given wavelength of light, and therefore a given energy level of the molecule struck by that light, the apparatus can detect whether the molecules of the species are in a stable energy state. Also, by measuring the quantity of trapping gas molecules created for a given amount of illumination of the species molecule at each wavelength of the light, one can determine the relative quantity of species molecules that enter each energy state. $SF_6$ and $CFCl_3$ are good trapping gases.

The novel features of the invention are set forth with particularity in the appended claims. The invention will be best understood from the following description when read in conjunction with the accompanying drawings.

DESCRIPTION OF THE PREFERRED EMBODIMENT

Figure 1:
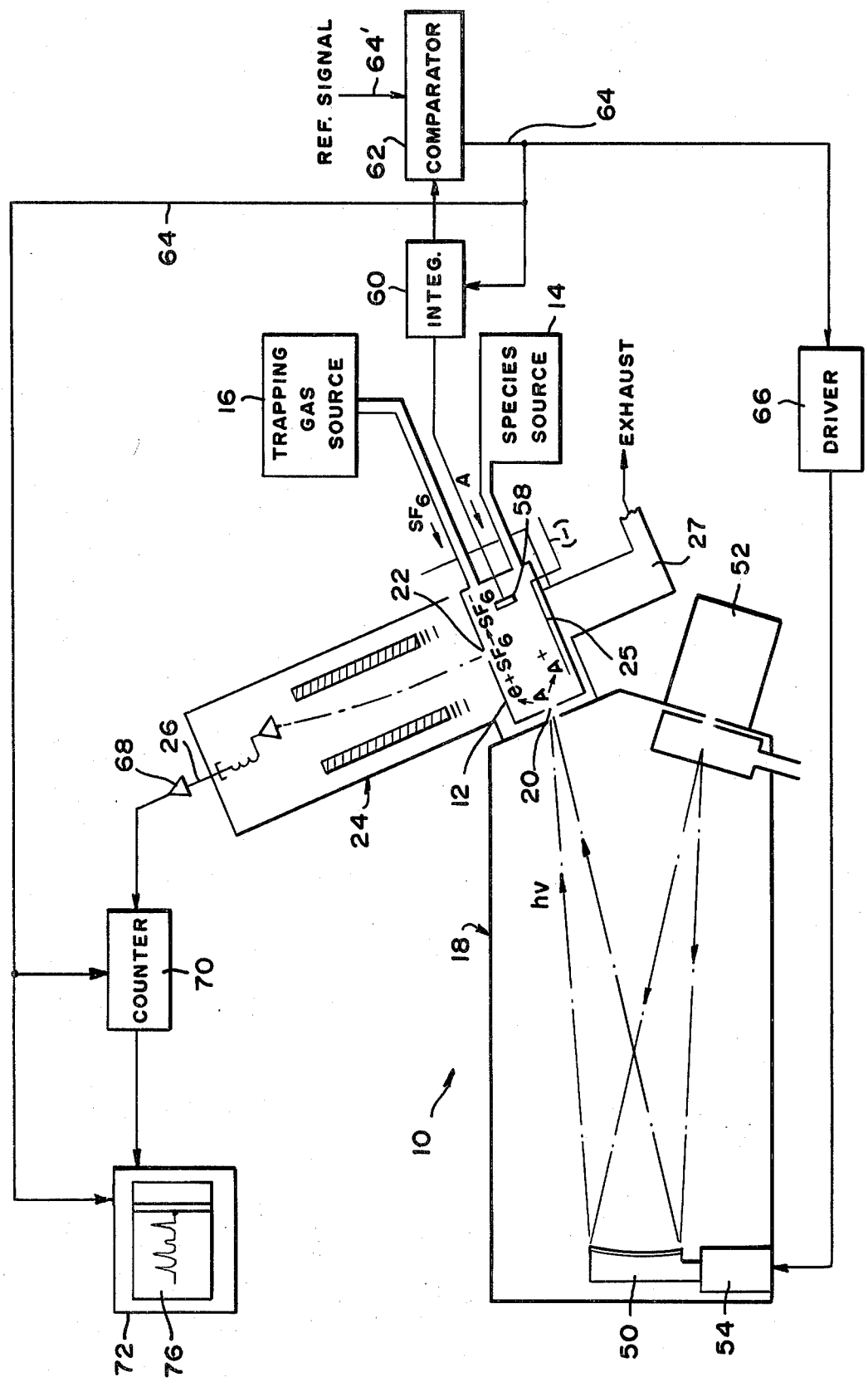
FIG. 1 is a schematic diagram illustrating the manner of operation of the invention.

FIG. 1 illustrates a spectra determining system 10 which includes a chamber 12 that receives a species of a gas to be analyzed and a trapping gas which aids in the analysis. The species is a gas containing atoms, molecules, or radicals that are all of the same type (i.e. all of the same species). The species to be analyzed, which is denoted by the letter A, may be referred to as a molecule in the following discussion, although it should be understood that it may be an atom or radical. The trapping gas is delivered to the chamber from a trapping gas source 16. A suitable trapping gas, and one which is indicated in the diagram of FIG. 1, is sulphur hexafluoride designated $SF_6$. The species to be analyzed A and the trapping gas $SF_6$ are both present in the chamber, when electromagnetic radiation such as light, of a narrow wavelength band, is delivered from a vacuum ultraviolet light monochromator through a slit-window 20 in the chamber. The photons of the light strike the species A to raise its energy level, and if the energy is raised above the ionization level of the species, then molecules of this species will be ionized.

In the ionization of a molecule of the species A, an electron is removed from the molecule, which results in the production of the positive ion $A^{30}$ and electron e. If the electron is of nearly zero energy level, it will be absorbed by a molecule of the trapping gas $SF_6$, to produce the negative ion $SF_6^-$. Thus, the process produces a negative ion of the trapping gas, $SF_6^-$. This negative ion $SF_6^-$ can pass out of the chamber through a slit opening 22 thereof into a mass spectrometer 24. Negative ions are repelled toward the opening 22 by a negatively charged electrode 25, while positive ions are attracted to the electrode. Neutralized and unionized species A and trapping gas $SF_6$ are pumped out of the chamber through an exhaust 27. The mass spectrometer 24 detects only the $SF_6-$ ions, and delivers a signal over an output line 26 whenever it detects such a trapping gas ion.

Figure 2:
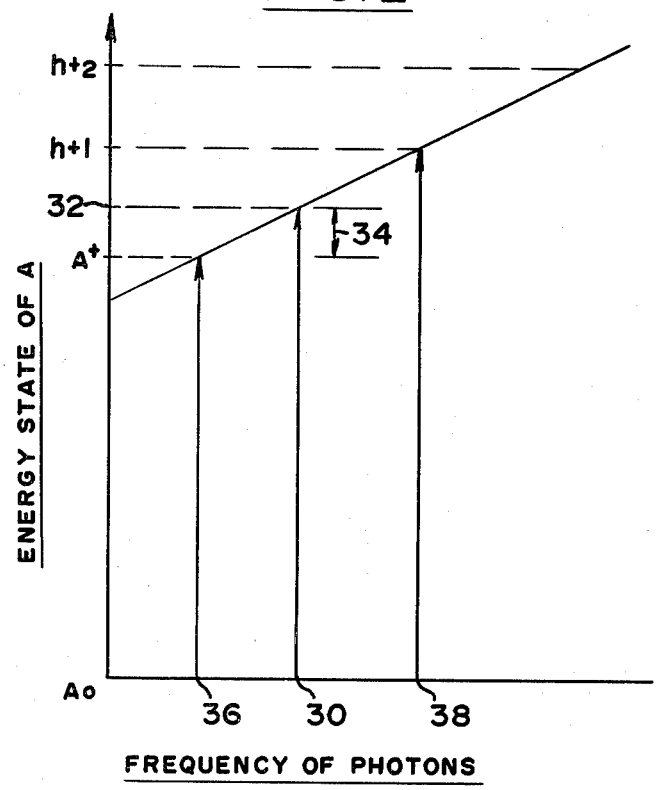
FIG. 2 is a graph showing the manner of operation of the apparatus of FIG. 1.

The particular trapping gas $SF_6$ has the characteristic that it absorbs an electron e only if that electron has substantially zero kinetic energy, that is, if the electron has an energy of less than 3 milli-electron volts (meV). FIG. 2 illustrates the manner in which the stable energy states of the species $A^+$ are detected. At a given frequency 30 of light photons, each photon can impart energy of an amount 32 to a species molecule, to raise it to the energy 32. This particular energy 32 is above the next lower energy state by a distance indicated at 34. Thus, when the molecule A is raised to energy 32, it quickly decays in energy to the next stable state $A^+$ while emitting an electron of the energy 34. This energetic electron will not be absorbed by a trapping gas molecule $SF_6$. Accordingly, this reaction will not result in the production of a negative ion of trapping gas, and the mass spectrometer will not detect such an ion.

If the frequency of the light is decreased to the level 36, then the photons of the light will strike a species molecule A and raise it to the first ionized level $A^+$. This will cause the molecule to emit an electron of substantially zero energy, and that electron will be absorbed by a trapping gas molecule to generate a trapping gas ion ($SF_6^-$) that will be detected by the mass spectrometer 24. Zero energy electrons will be similarly generated if the frequency of the light is increased to the level 38. Photons of light of the frequency 38 will strike a species molecule A and raise it to stable energy state $n+1$ which is some higher stable energy state and which is perhaps several volts above the ionization level $A^+$. As a result, the species molecule will emit an electron which will have substantially zero energy and therefore will be absorbed by a trapping gas molecule which will be detected by the mass spectrometer. Thus, only those light frequencies such as 36 and 38 which raise the species to stable energy states, will result in the detection of large numbers of trapping gas ions by the msss spectrometer. On the other hand, light frequencies which ionize species with energy between stable energy levels, produce high energy electrons which result in no detectable signal.

Figure 3:
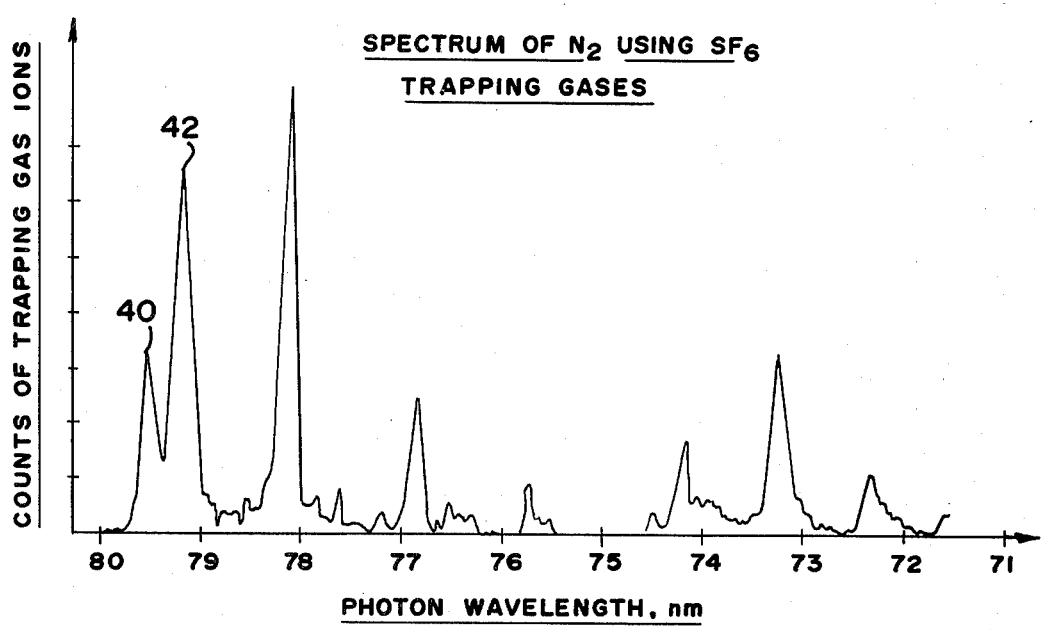
FIG. 3 is a graph showing the threshold spectrum of nitrogen molecules obtained with the apparatus of FIG. 1.

FIG. 3 illustrates the spectrum of nitrogen molecules $N_2$. This is a graph obtained from the apparatus of FIG. 1, which results when the wavelength of the light is gradually changed and the number of trapping gas ions per second is recorded at each light frequency. It can be seen that at a wavelength slightly over 79 nm (nanometers) large count rates of trapping gas ions are detected at the peak 40, indicating that this is the ionization potential of nitrogen. A next stable energy state is indicated by the peak 42, etc. Thus, a graph can be constructed indicating the stable energy states of the species, and the strength of excitation to each state. It may be noted that the terms, energy "level" and energy "state," are commonly used to denote stable energy states.

In the apparatus of FIG. 1, the frequency of light reaching the window 20 of the chamber 12 is varied by slowly tilting a grating 50 of the monochromator, which diffracts light from a discharge lamp 52 towards the window 20. The intensity of the light reaching window 20 may unintentionally change as its frequency changes, in main part due to variations in the spectral output of the lamp 52. To compensate for such variations, a light sensor 58 is provided which senses the intensity of light directed into the chamber 12. The output of the sensor 58 is proportional to the intensity of the light (i.e. number of photons striking the sensor per unit time at that grating position). The output of the sensor 58 is delivered to an integrator 60 which delivers a count to a comparator 62. When the comparator 62 senses that the output of the integrator 60 equals the level of a preset reference count 64', so that the total number of photons has reached a predetermined level, the comparator delivers a reset signal over line 64 to the integrator 60 to reset it, and also delivers a signal to a driver 66 that operates the grating tilting mechanism 54 to tilt the grating 50 by a predetermined angle which will shift the light frequency by a predetermined step. Thus, the circuit assures that the same amount of light energy is delivered to the chamber 12 for each frequency step of the light.

The output line 26 of the mass spectrometer 24 contains a series of pulses, with each pulse indicating the detection of one negative ion of the trapping gas. This output on line 26 is delivered through an amplifier 68 to an integrator or counter 70. The counter 70 delivers its signal to a recording mechanism such as a recorder 72 that plots a graph 76. The height of the pen of the recorder is proportional to the final counts in the counter 70, to indicate the number of detected trapping gas ions at each frequency of the ionizing light. The resetting signal on line 64 from the comparator 62 is delivered to the counter 70 to reset it, and to the chart recorder 72 to advance it, whenever the grating 50 of the monochromator 18 is tilted by a step to change the frequency of the light. In this way, the height of the graph or chart 76 is proportional to the counts of negative ion signal per preset number of photon counts at each wavelength of ionizing light. In this way, effects of variations, with wavelengths, of light intensity reaching slit window 20 are removed.

As mentioned above, the molecule $SF_6$ has been found to be very useful as a trapping gas in the apparatus of FIG. 1, inasmuch as it will absorb electrons only if the electrons have almost zero kinetic energy. Another molecule that can be used is $CFCl_3$ which is often referred to as Freon-11. The Freon molecule also absorbs an electron only if that electron is of an energy level very close to zero. It may be noted that when a Freon molecule absorbs an electron, the molecule is dissociated into a negative ion $Cl^-$ plus a radical $CFCl_2$. Thus, a $CFCl_3$ molecule undergoes a dissociative attachment process when it accepts an electron. The negative chlorine ion which is produced can be detected with the same apparatus shown in FIG. 1. Thus, for the two trapping gases $SF_6$ and $CFCl_3$, the reactions are as follows:

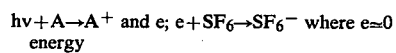

$hv + A \rightarrow A^+$ and e; $e + SF_6 \rightarrow SF_6^-$ where $e \approx 0$ energy

$hv + A \rightarrow A^+$ and e; $e + CFCl_3 \rightarrow Cl^- + CFCl_2$ where $e \approx 0$ energy where hv is the energy of a photon, A is a species molecule, $A^+$ represents an ionized species molecule in a stable energy state at or above the ionization level, e is an electron, and $SF_6^-$ and $Cl^-$ are the negative ions of $SF_6$ and Cl, respectively.

It is possible to use trapping gases that accept only electrons within a narrow energy band which is above zero, rather than near zero. In that case, the detection of an electron indicates that the species has an energy state equal to that of the photon minus the kinetic energy of the absorbed electron. However, of the trapping gases which have been tested by the inventors hereof, and which accept electrons within a narrow band above zero electron energy, all had much wider bands than the molecules $SF_6$ and $CFCl_3$ whose acceptance bands are narrow and are at nearly zero energy. $SF_6$ and $CFCl_3$ both appear to have acceptance bands of zero to 3 meV.

Thus, the invention provides a method and apparatus for measuring the ionization potentials, and stable energy states equal to and above the ionization potential, of an atom, molecule, or radical species, with high precision. This is accomplished by the use of a trapping gas which accepts only molecules within a narrow band of energy. The trapping gas molecules are positioned adjacent the species being investigated, and ionizing energy of a predetermined level is applied to the species, as by irradiating the species with light of a narrow wavelength bandwidth. The number of trapping gas ions which are detected, (for a preset number of photons) as by a mass spectrometer, indicates the strength of excitation (ability to absorb light or other energy) of the species at any particular energy level to which the species has been raised.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for detecting the stability of energy states of a gaseous species, comprising:
   adding a trapping gas which absorbs electrons only of a narrow energy band, to said species;
   applying photo ionizing energy of a controlled level to said species to cause said species to lose an electron so that the electron can be absorbed by at least a component of said trapping gas if the electron has an energy within said narrow band; and
   detecting the ionized quantity of said at least a component of said trapping gas, thereby to detect the relative stability of the species when raised to an energy level equal to the ionizing energy minus the electron energy band.

2. The method described in claim 1 wherein:
   said step of ionizing includes applying light to said species, and varying the wavelength of the light; and
   said step of detecting includes detecting the quantity of said at least component at different light wavelengths.

3. The method described in claim 2 including:
   detecting the intensity of said light, and maintaining said light at each wavelength, so that the integral of light intensity with time is the same at all light wavelengths.

4. The method described in claim 1 wherein:
   said trapping gas is $SF_6$.

5. The method described in claim 1 wherein:
   said trapping gas is $CFCl_3$.

6. Apparatus for detecting ionization potentials and the stability of energy levels of gas species, comprising:
   means for adding a trapping gas which absorbs electrons only within a narrow kinetic energy band, to said species;
   means for applying photo ionizing energy to the species gas when it is combined with said trapping gas; and
   means for detecting the quantity of negatively ionized trapping gas produced upon the operation of said energy-applying means thereby to detect the relative stability of the species when raised to an energy level equal to the ionizing energy minus the electron energy band.

7. The apparatus described in claim 6 wherein:
   said means for applying ionizing energy applies light of a narrow wavelength band to said species; and includes means for changing the wavelength of said band; and including
   means responsive to the integral with time of the light intensity applied by said applying means, for changing the wavelength of the band of light to applying substantially the same integral of light intensity with time at each wavelength.

8. A method for measuring the stability of the energy state spectrum of a gaseous species, comprising:
   positioning a trapping gas that absorbs only electrons having an energy within a narrow band, adjacent to said species;
   applying photon radiation of a narrow energy band to said species; and
   detecting negative ions of said trapping gas thereby to detect the relative stability of the species when raised to an enerby level equal to the ionizing energy minus the electron energy band.

9. The method described in claim 8 wherein:
   said trapping gas is chosen from the group of $SF_6$ and $CFCl_3$.

10. Apparatus for detecting the stability of the energy state spectrum of a gaseous species, comprising:
    walls forming a chamber having an exit opening for discharging negative ions;
    means for applying a trapping gas that absorbs only electrons having an energy within a narrow band, to said chamber, and for applying a species to be tested to said chamber;
    means for applying photon radiation of a narrow energy band to said chamber; and
    a mass spectrometer coupled to said exit opening of said chamber, for detecting negative ion of said trapping gas, thereby to detect the relative stability of the species when raised to an energy level equal to the ionizing energy minus the electron energy band.

* * * * *